United States Patent [19]

Lewyn

[11] 4,260,951

[45] Apr. 7, 1981

[54] MEASUREMENT SYSTEM HAVING POLE ZERO CANCELLATION

[75] Inventor: Lanny L. Lewyn, Laguna Beach, Calif.

[73] Assignee: Hughes Aircraft Company, Culver City, Calif.

[21] Appl. No.: 6,983

[22] Filed: Jan. 29, 1979

[51] Int. Cl.³ .............................................. H03K 5/00
[52] U.S. Cl. .................................. 328/165; 128/690; 307/311; 328/2
[58] Field of Search ............................... 128/687-690; 328/2, 165, 167; 307/231, 311; 250/214 A, 214 AL, 214 B, 214 C, 215

[56] References Cited

U.S. PATENT DOCUMENTS 3,657,669   4/1972   Proakis .................................. 328/167

OTHER PUBLICATIONS

"Infrared Sensor Built into Watch Measures Wearer's PR", (Anon), Electronics Review vol. 50, No. 9, Apr. 28, 1977.

Guillermin, E. A., "Synthesis of Passive Networks", John Wiley & Sons, Inc., New York, 1957. pp. 86, 232, 521-522.

Nowlen, C. H. et al., "Elimination of Undesirable Undershoot in the Operation & Testing of Nuclear Pulse Amplifiers," The Review of Scientific Instr., vol. 36, No. 12, Dec. 1965, pp. 1830-1839.

Primary Examiner—Robert W. Michell
Assistant Examiner—Francis J. Jaworski
Attorney, Agent, or Firm—W. H. MacAllister; Walter J. Adam

[57] ABSTRACT

A pulse IR reflectance plethysmograph system for heart rate measurement and display in a digital watch or as a medical instrument having a novel direct coupled pole zero cancellation circuit that compensates undesirable shaping effects on the heart blood pressure wave. The system utilizes a pulsed LED light emitting diode for transmitting light pulses and a photodiode for receiving light pulses reflecting from a finger.

6 Claims, 11 Drawing Figures

MEASUREMENT SYSTEM HAVING POLE ZERO CANCELLATION

A photodiode is connected directly to a signal conditioning circuit which rapidly removes unwanted asynchronous ambient background light signals such as from sunlight, by means of a switched ambient light subtractor circuit. The signal current after cancellation of the ambient background signal is sampled in an integrate and hold circuit to provide a heart systolic pressure wave or envelope of the pulse amplitudes. The synchronous steady state IR pulse carrier envelope signal is cancelled by a perfect second-order feedback loop via an integrating amplifier and a switched transconductance element that operates with fast response, even under conditions of large overloads that occur at the sensor. The second-order feedback loop because of various restraints, necessarily has a long differentiation time constant. The pole zero cancellation circuit which is included in an amplifier circuit cancels the long differentiation time constant so as to remove undesired shaping of the heart pressure wave caused by the second-order loop. Thus, a heart pressure wave which has been shaped by a double differentiation with only a short time constant is provided at the output of the amplifier circuit. Pulses of the heart systolic pressure wave are then detected with a high degree of timing accuracy to determine the pulse rate which is then displayed.

BACKGROUND OF THE INVENTION

This invention is related to pulse rate measurement systems, and particularly to an improved pulse rate measuring system that includes input coupled pole zero cancellation to rapidly and accurately develop pulse rate readings.

In a patent application, Ser. No. 965,816, entitled Heart Rate Measurement System, invented by Lanny L. Lewyn and filed Dec. 5, 1978, the same inventor on this application, a pulsed IR plethysmograph was disclosed and claimed having a photodiode and a gated circuit connected thereto for pulse-by-pulse cancellation of the asynchronous ambient light components of the photocurrent signal. A switched integrate and hold circuit was provided to respond to the current signal after ambient light cancellation to provide a signal representive of the blood pressure modulation. A switching transconductance element, an integrating operational amplifier and the integrate and hold circuit were included in a perfect second-order feedback loop to develop current pulses for cancellation of synchronous IR carrier steady state photocurrent resulting from the pulsed light source. Because of the size restraints on certain elements in the system and the objective of keeping individual stage DC gains low, especially in a watch, the differentiation in the perfect second-order loop necessarily had a relatively large time constant. The result of this long time constant differentiation was an undesirable shaping effect on the heart pressure wave at the output of the loop so that the amount of pulse rate uncertainty was greater than might have been desired. An arrangement as shown and described in the above-referenced patent application that would remove the effect of this long time constant third differentiation and result in a system with only double differentiation with a short time constant would be a substantial advance to the art.

Pole zero cancellation is generally known in network theory, at least as to remaining poles at the limits, as discussed in the book by E. A. Guillermin, *Synthesis of Passive Networks,* John Wiley and Sons, Inc., New York, 1957. Also, in the nuclear field, pole zero cancellation has been applied to some of the problems of pulse shaping in nuclear pulse amplifiers, as discussed in a paper by C. H. Nowlen and J. L. Blankenship published starting with page 1830 in the *Review of Scientific Instruments,* 1965 edition, Vol. 36, No. 12. This paper shows a system operating with a charge sensitive preamplifier that has overload conditions resulting from high energy particles that deposit a large amount of energy on the detector causing the charge sensitive preamplifier to go into an overload condition. The pole zero cancellation in in the system of the paper is to cancel the effect of the slow recovery of the charge sensitive preamplifier so that information can be reliably extracted from a single pulse. The objective of applicant's compensation by pole zero cancellation is different than taught in the prior art in that Applicant's system operates with DC coupling to a perfect second-order loop which has the purposes of suppressing the individual pulse of the pulse carrier and extracting only the information from variations in pulse-to-pulse amplitude. Thus, Applicant's compensation operates in a time frame that is slow compared to the pulse-to-pulse time interval. In contrast to Applicant's system, the nuclear pulse amplifier system of the paper uses pole zero cancellation to discard the remnants of a pressure pulse so that the system is totally cleaned when the next pulse is received. Further, Applicant's invention is to prevent excess noise and an undesirable shaping effect in the heart blood pressure wave which would lead to improper timing information while the pole zero cancellation in the paper is used primarily for measuring pulse amplitude rather than time. Accordingly, Applicant's type of compensating circuit including its function, is direct coupling to the signal source and its arrangement in conjunction with a perfect second-order loop input is not taught in the prior art.

SUMMARY OF THE INVENTION

In an exemplary embodiment of the invention, a pulsed IR reflectance plethysmograph for heart rate measurement includes a signal processing circuit providing a heart pressure wave that is filtered with a differentiation having a relatively large time constant because of the restraints on the component values such as resulting from the chip size in a digital watch. To overcome this long time constant differentiation, a novel amplifier arrangement is directly coupled to the signal processing circuit and includes a pole cancelling arrangement to effectively substitute a short time constant differentiation for the long time constant differentiation. To avoid high gain DC coupling in the amplifier, two short time constant coupling networks must be used. Triple differentiation produces undesireable signal shaping and signal-to-noise characteristics. Therefore, the input signal processing circuit differentiation must be cancelled and it is simpler to accomplish this if it has a long differentiation time constant rather than a short one. The system has a pulsed light source applying the pulses of light to a finger, for example, for reflection to a detector such as a photodiode. A gated circuit is connected directly to the photodiode for pulse-by-pulse cancellation of the asynchronous ambient light components of the photocurrent signal. A switched integrate and hold circuit is provided to respond to the current signal after ambient light cancellation to develop a signal representative of the blood pressure modulation. A perfect second-order loop is formed including the integrate and hold circuit, an integrating operational amplifier and a switched transconductance element, and develops current pulses for cancellation of synchronous IR carrier steady state photocurrent resulting from the pulsed light source. The integrating operational amplifier includes a resistor $R_B$ and a capacitor $C_B$ for providing the differentiation time constant to the system response. The amplifier and filter circuit includes an operational amplifier directly coupled to the integrate and hold circuit through a differentiating capacitor and resistor. A bypass resistor $R_3$ is coupled in parallel to the differentiating capacitor $C_1$ to provide a time constant $R_3 C_1$ equal to $R_B C_B$. The bypass resistor $R_3$ provides a zero to cancel the pole caused by the $R_B C_B$ differentiation with the result that a short time constant differentiation $(R_1 \| R_3).C_1$ is substituted for the large time constant differentiation. As a result, the shaped heart wave signal amplifier output has a high degree of systolic pressure wave pulse-to-pulse timing accuracy and a reliable pulse interval can be detected for displaying the pulse rate.

It is therefore an object of this invention to provide an improved pulse rate measurement system.

It is a further object of this invention to provide a plethysmograph for heart rate measurement that rapidly provides a substantially accurate pulse count.

It is another object of this invention to provide a circuit for a pulse watch that maintains high AC gain in each stage while holding DC stage gain low and yields double differentiation shaping instead of the triple differentiation shaping which would otherwise be the result of AC coupling three high gain stages.

It is another object of this invention to maintain low DC stage gains within the component size limitations imposed by the constraints of a circuit which is mounted on a wristwatch.

BRIEF DESCRIPTION OF THE DRAWINGS

These and other objects, features and advantages of the invention itself, will become apparent to those skilled in the art in the light of the following detailed description taken in consideration with the accompanying drawings, wherein like reference numerals indicate like corresponding parts throughout the several parts wherein:

FIG. 2 is a schematic circuit diagram of the asynchronous ambient light cancellation circuit shown in the system of FIGS. 1 and 1a;

FIG. 6 is a schematic diagram of waveforms of voltage and current as a function of time for further explaining the operation of the system of FIGS. 1 and 1a;

DESCRIPTION OF THE PREFERRED EMBODIMENTS

Figure 1:
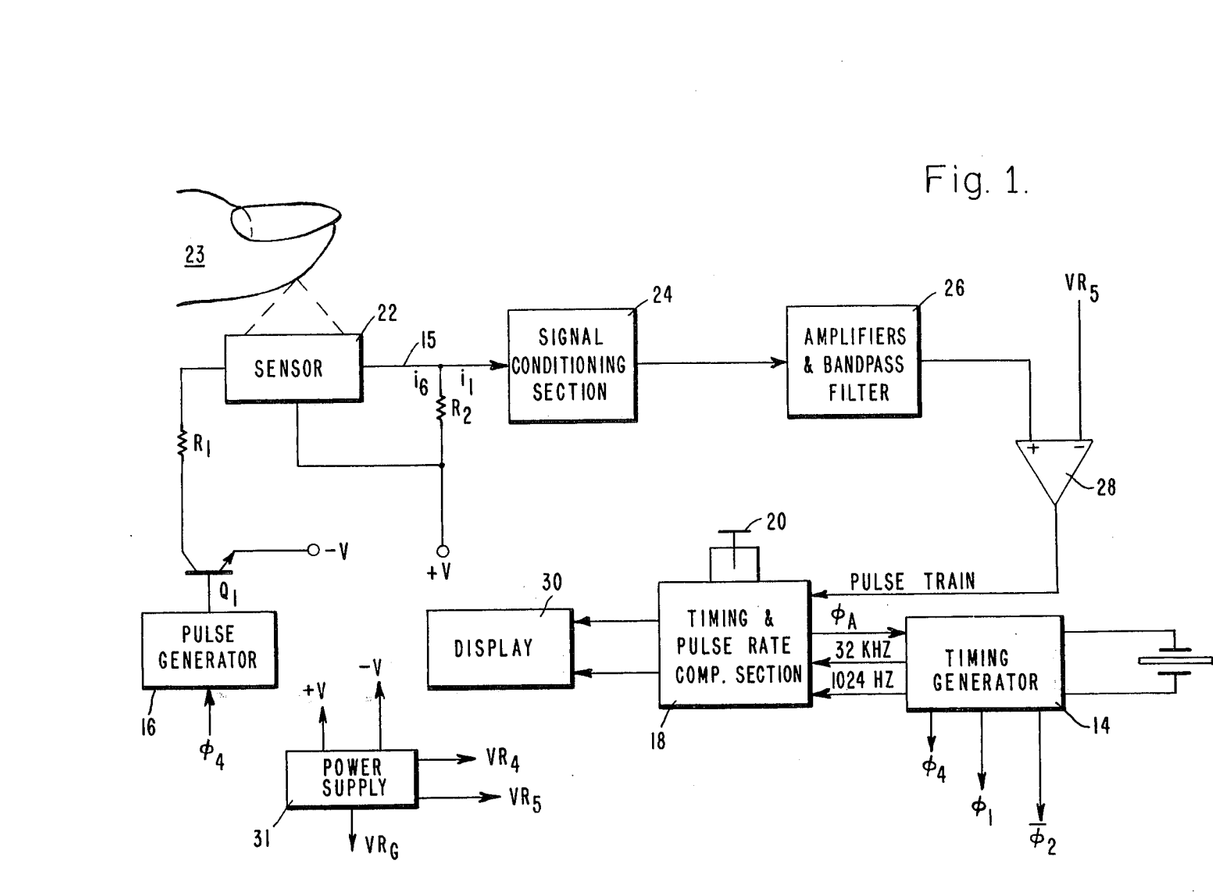
FIG. 1 is a schematic block diagram of a pulsed IR reflectance plethysmograph system for heart rate measurements illustrated in a wristwatch as an example of one use of the system in accordance with the invention.
Figure 1A:
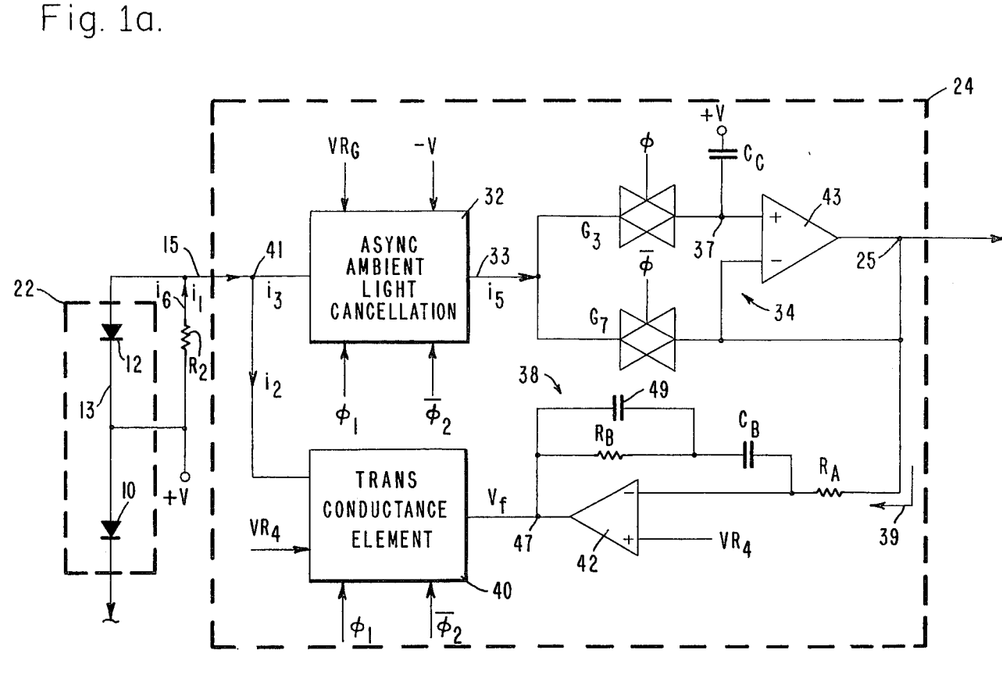
FIG. 1a is a schematic circuit and block diagram showing a sensor and the current conditioning section of FIG. 1 in further detail.

Referring first to FIGS. 1 and 1a, one embodiment of the invention is incorporated in a plethysmograph adapted to fit in the case of a digital wristwatch for use in field measurements of heart rate, such as by a jogger immediately upon stopping, or while resting, for use by a person who must measure his heart rate frequently, or for use by medical or related personnel. It is to be understood that the principles of the invention are not limited to wristwatches but also apply to instruments that may have other forms such as those that may be desirable for field or hospital uses. More particularly, the illustrated system which includes the compensating combinations of the invention, is a heart rate measurement device which uses the IR reflectometer principle for peripheral pulse measurement by sensing volumetric variations of the capillaries of the fingers or of any tissue with sufficient capiliary development to provide a useful light absorption signal. It is to be noted that the system in which the invention is incorporated includes operation at any suitable IR or other wavelengths at which there is suitable penetration through tissue to respond to the blood pressure variations and is not be limited to any particular wavelength band. The illustrated system utilizes an infrared (IR) light emitting diode (LED) 10 to provide a pulsed source of IR light which is reflected off of the tissues of the finger, for example, and onto a photodiode detector diode 12 having a photocurrent response characteristic. The peripheral systolic wave causes an abrupt increase in IR light absorption (the reflectance drops) by the capillaries of the finger which dilate in response to the systolic pressure wave. The small (~2%) changes or modulation in reflected light amplitude is sensed by the photodiode 12 along with the steady state component of the reflected IR light pulse train plus ambient light from any other source such as sunlight or indoor lighting. To avoid the problems of an LED drive feedback system, the LED 10 is driven in an open loop with constant current pulses so that the LED drive and front end gains are therefore set at optimum levels and these levels do not and need not change as a result of beackground lighting conditions or tissue reflectivity. The LED 10 is driven at a fixed rate set by timing or clock pulses $\phi_4$. A crystal oscillator and pulse system timing generator 14 provides the timing pulses $\phi_4$ which are typically at 73 Hz (to insure that the beat frequencies between the 73 Hz sampling frequency and the indoor lighting frequencies are well above the system passband) to a base current pulse generator 16, which in turn applies pulses to the base of an NPN type drive transistor $Q_1$. The emitter of the transistor $Q_1$ is coupled to a negative supply voltage, $-V$, and the collector is coupled through a resistor $R_1$ to the cathode of the LED 10. The anode of the LED 10 is coupled through a lead 13 to the positive supply voltage, $+V$, and to the cathode of the photodiode 12 which in turn has its anode coupled to a lead 15. A resistor $R_2$ is connected to the $+V$ supply (lead 13) and to the lead 15. The transistor $Q_1$ conducts pulses of current through the LED 10 and through the current limiting resistor $R_1$ when an analog power control signal $\phi_A$ is turned on. A digital watch timing and pulse rated computation section 18 of a digital watch provides the control signal $\phi_A$ to the timing generator 14 once the operator depresses a push button switch 20. When the switch 20 is depressed a second time, the control signal $\phi_A$ is then turned off. The LED 10 in the illustrated watch system, is mounted in a small sensor 22 illustrated as a dotted box on the face of the watch to pass or transmit IR pulses to the surface of a finger 23, for example, of the person whose pulse rate is being monitored. The IR pulses reflected off the tissue and capillaries of the finger 23 are received by the photodetector 12, also mounted in the sensor 22. The timing generator 14 which responds to a crystal oscillator as is well known in the art, provides the timing signal $\phi_4$ as well as timing signals $\phi_1$ and $\overline{\phi}_2$ for use in the system. Also, the timing generator 14 applies suitable signals such as a 32 KHz clock signal and 1024 Hz signal to the computation section 18.

An input signal current conditioning section 24 directly coupled to the photodiode anode through the lead 15, cancels asynchronous ambient light (sunlight, or artificial light as well as other light asynchronous to the system) and synchronous steady state components of the LED light pulse carrier. The output of the signal conditioning section 24 passes through a node 25 to an amplifier and bandpass filter 26 as a heart pressure wave voltage having systolic pulses occurring at a rate that is typically 60 to 80 per minute but which can also be as high as 199 pulses per minute. The amplifier and bandpass filter 26 includes the compensating arrangement that in combination with the section 24 provides the highly accurate pulse counting system in accordance with the invention. A voltage level discriminator 28 which provides a comparison of the heart pressure wave voltage relative to the threshold voltage $VR_5$, detects these systolic pulses from a signal provided by the amplifier and bandpass filter 26, and transmits a pulse train of rate determining pulses to the digital watch timing and pulse rate computation section 18 which detects the time (T) between the edges such as the positive going leading edges of the systolic pulses in the train, and computes the pulse rate R ($R=I/T$, with $I=$ the total timing interval). The type of computations provided by the section 18 is well known in the digital art and need not be explained in further detail. The pulse rate R is then displayed as a decimal number by a digital watch display section 30.

A suitable power supply such as a battery power supply 31 is provided and may include a pair of batteries (not shown) that together provide a voltage of approximately 3.2 volts between the voltages $+V$ and $-V$ as utilized in the illustrated heart rate monitoring system in a watch. The power supply 31 also provides voltages $VR_4$, $VR_5$ and $VR_G$. The voltage $VR_5$ for the discriminator 28 is provided for example, by a series string of five diodes, coupled between $+V$ and a constant current generator source with the voltage $VR_5$ being provided at the cathode of the diode that is coupled to the constant current source. The voltage $VR_4$ is the voltage at the anode of the last diode that is coupled to the constant current source. It is to be noted that the discriminator 28 triggers on any signal from the amplifier and bandpass filter 26 that exceeds the difference between the discriminator reference voltage $VR_5$ and the amplifier quiescent output voltage $VR_4$. The voltage $VR_4-VR_5$ is typically one diode drop or approximately 0.5 volts.

The input current conditioning section 24 includes an asynchronous ambient light cancellation circuit 32 coupled to the lead 15 to receive a photocurrent $i_3$ which is a current $i_1$ as provided by the photodiode 12 (and a small current $i_6$ from the diode bias resistor $R_2$) combined at a node 41 with the synchronous carrier supression current $i_2$. The ambient light current cancellation circuit 32 also receives the reference voltage $VR_G$ and the timing pulses $\phi_1$ and $\overline{\phi}_2$ for providing carrier cancellation during the sampling pulse periods, and applies an output current $i_5$ on a lead 33 to an integrate and hold circuit 34. Gates $G_3$ and $G_7$, an integrate and hold capacitor $C_c$ and a unity gain amplifier 43 are all included in the integrate and hold circuit 34. The gate $G_3$ responsive to timing signal $\phi_1$ for being biased into conduction is coupled between the lead 33 and a node 37 which in turn is coupled to a positive input terminal of the unity gain amplifier 43. The capacitor $C_c$ is coupled between a $+V$ terminal and the node 37 to provide integration of the signal for applying a blood pressure wave to the node 25. A gate $G_7$ is coupled between the lead 33 and the negative feedback input terminal of the unity gain amplifier 43, as well as to the node 25. The gate $G_7$ is biased into conduction in response to the timing signal $\overline{\phi}_2$ to prevent the parasitic capacitance in the circuit at the lead 33 from being charged during the interval between LED pulses.

A perfect second order feedback loop 39 includes an operational integrator 38, a resistor $R_A$, an integrating capacitor $C_B$, a stabilizing resistor $R_B$, an integrating operational amplifier 42, and includes a switched capacitor transconductance element 40, for providing the current $i_2$ to or from the node 41 at the lead 15. The resistor $R_A$ is coupled between the node 25 and a negative feedback terminal of the amplifier 42, with the negative terminal feedback being derived serially through the integrating capacitor $C_B$ and the stabilizing resistor $R_B$ in turn coupled to a lead 47 at the output of the amplifier 42. A high frequency bypass capacitor 49 is connected across the resistor $R_B$. A reference voltage $VR_4$ is applied to the positive input terminal of the operational amplifier 42. The switched capacitor transconductance element 40 receives the amplifier 42 output signal $V_f$ on the lead 47, the reference voltage $VR_4$ and the timing pulses $\phi_1$ and $\overline{\phi}_2$, to provide the $i_2$ correcting current to the node 41 which cancels the steady state component of the synchronous pulse carrier as well as corrects any residual imbalance remaining after ambient light cancellation by the circuit 32.

To further explain the overall operation of the system including the combinations of the invention, the illustrated base current pulse generator 16 provides a 31 μs pulse of 2 mA to the base of the drive transistor $Q_1$ every 13.67 μs i.e., at a 73 Hz rate. The photodiode current is rotated to the input signal conditioning section 24 where ambient background light and the synchronous steady state component of the LED light pulse carrier are removed by cancellation. The heart pressure wave voltage signal which is the envelope of the detected photocurrent pulses, is processed by the amplifier and bandpass filter 26 to compensate for the filtering in the section 24 as well as to remove any remaining finger motion artifact signal and any background light signals which have not been completely cancelled by the input signal conditioning circuit 24. The voltage level discriminator 28 triggers on any amplifier output greater than the difference between two reference voltages $VR_5$ and $VR_4$ to apply a pulse train to the computation section 18.

Figure 2:
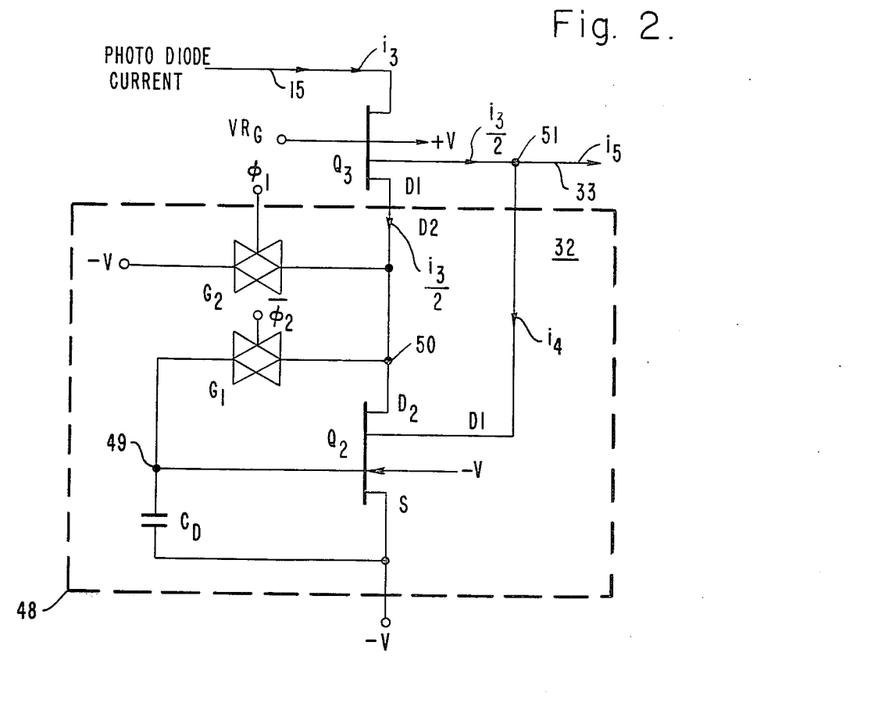

The input signal conditioning section 24 will now be explained in further detail starting with the asynchronous ambient light cancellation function which is carried out by a split-drain P channel MOS field effect transistor $Q_3$ and the circuit of a dotted line block 48 as shown in FIG. 2. Operation of the ambient light cancellation circuit 32 may best be understood by first describing that portion of the circuit enclosed in the block 48 which functions as a "storage current mirror" to maintain drain current $i_4$ to a drain electrode $D_1$ of a split-drain N-channel MOS fieldeffect transistor (FET) $Q_2$, approximately equal to the drain current $i_3/2$ in a drain electrode $D_2$ of the split-drain P-channel FET $Q_3$, so long as a transmission gate $G_1$ is open (conducting) and a transmission gate $G_2$ is closed (not conducting). The split-drain FET $Q_3$ has its gate electrode coupled to a voltage reference terminal $VR_G$ and its substrate biased to $+V$ volts. The photodiode current is applied directly to the source electrode of the FET $Q_3$ without amplification or conversion of another electrical parameter and drain electrode $D_1$ thereof is directly connected to the output current lead 33. The gate $G_1$ responsive to the timing signal $\overline{\phi}_2$ is coupled between a gate node 49 and a node 50, the latter node being coupled between the drain electrode $D_2$ of the FET $Q_3$ and a drain electrode $D_2$ of the FET $Q_2$. Also, a gate $G_2$ responsive to the timing pulse $\phi_1$ is coupled between the negative supply voltage $-V$ and the node 50. The drain electrode $D_1$ of the FET $Q_2$ is coupled to a node 51 and the output lead 33 and the source electrode of the FET $Q_2$ is coupled to the negative supply $-V$ voltage terminal. The well of the FET $Q_2$ is biased by the voltage $-V$. A capacitor $C_D$ is coupled between the gate node 49 and the $-V$ voltage supply. When the transmission gate $G_1$ is conducting, the current $i_4$ is equal to the drain electrode $D_2$ output current of the FET $Q_3$, which is $i_3/2$, and the potential of the node 49 follows the potential of the gate node 50. The drain current from the FET $Q_3$ to the node 51 is half of the current $i_3$ because the FET $Q_2$ is constructed so that both drain currents are always equal to each other when a sufficient source to drain voltage potential is maintained. The current $i_3/2$ applied to the drain electrode $D_2$ of the FET $Q_2$ establishes the current $i_4$ in the drain electrode $D_1$ of the FET $Q_2$ during the interpulse intervals between sampling pulses, which current must be equal. It is to be noted that the capacitor $C_D$ which is coupled between the gate electrode and the source electrode of the FET $Q_2$ assumes a charge to bias the FET $Q_2$ to pass the current $i_3/2$ while the gate $G_1$ is conducting. If the gate $G_1$ is closed (non-conducting) while the switch $G_2$ is opened (conducting) the voltage $-V$ is applied to the node 50 so that that drain electrode $D_1$ of the FET $Q_3$ remains conducting even though the current increases. Also, the current $i_4$ remains at a value equal to its value just before the sample pulse period. The constant current $i_4$ results from the charge stored on the capacitor $C_D$ maintaining the same gate voltage across the FET $Q_2$ as that prior to the sample pulse period, so that the total current $i_4$ into the drain electrode $D_1$ of the FET $Q_2$ does not change during the sample pulse period. The $-V$ voltage at the drain electrode $D_2$ of the FET $Q_3$ maintains that FET in the balanced split-drain mode during the sample pulse period so that the current applied to the node 51 therefrom is the $i_4$ current plus one-half of the additional signal current. The output current $i_5$, during the sample period, is just the difference between the drain $D_1$ current of the FET $Q_2$ and the drain $D_1$ current of the FET $Q_3$. If the $i_4$ ambient current remains essentially constant and the steady state pulse envelope and other imbalances are cancelled, the output current $i_5$ is then just one-half of the sampling period signal current (heart pressure wave). During the sample pulse period, the current into the drain electrode $D_2$ of the FET $Q_2$ is essentially zero, the drain electrode $D_2$ current from the FET $Q_3$ passing through the gate $G_2$ to the negative supply.

To further explain the operation including the cancellation of ambient photocurrent, when the LED pulse controlled by a timing signal $\phi_4$ is first applied to the pulse generator 16 (FIG. 1), the gate $G_1$ is biased out of condition and the drain current $i_3/2$ to the node 50 from the FET $Q_3$ increases as a result of the LED light pulse sensed by the photodiode 12 (FIG. 1). If the background (ambient) light will remain nearly constant during the brief 31-microsecond pulse ($\phi_4$) that triggers the LED on, the ambient light current will be cancelled since the current $i_4$ remains constant (due to the stored charge on the capacitor $C_D$) and is equal to the ambient light photodetector current $i_3/2$ applied to the node 51 between the LED pulses. The true or total LED current signal which includes the synchronous steady state sample pulse envelope is split into equal parts by the FET $Q_3$, and half is applied to the node 51, the half including the current $i_5$ which is the current in excess of the ambient light current $i_4$. The excess current $i_5$ charges the integrate and hold capacitor $C_c$ through the transmission gate $G_3$ during LED sample pulse periods.

Figure 3:
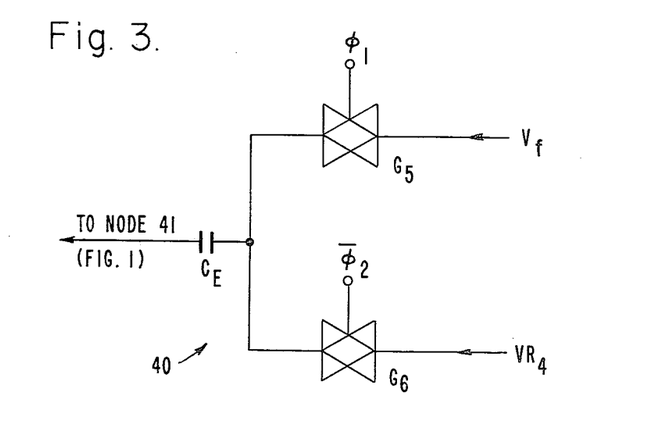
FIG. 3 is a schematic circuit diagram of the switched capacitor transconductance element shown in a perfect second-order feedback loop in the system of FIGS. 1 and 1a for synchronous steady state pulse carrier light cancellation.

Without the synchronous LED light cancellation circuit of FIGS. 1, 1a and 3, the LED reflected light current would quickly charge and maintain the charge on the capacitor $C_c$ and the voltage at the node 37 (FIG. 1) would be driven to and remain at a high potential close to the $+V$ supply voltage. That high potential condition on the capacitor $C_c$ is precisely what happens a fraction of a second after the finger is placed over the window 22 (FIG. 1) of the sensor and before the synchronous carrier pulse current cancellation control loop 39 including the circuit of FIG. 3 has responded. After the switched capacitor transconductance element 40 of FIG. 3 has had time to respond, the steady state component of the reflected LED light pulse carrier, as well as any residual imbalance from the cancellation circuit of FIG. 2 or unity gain amplifier 43, are cancelled. Thus, the output current $i_5$ consists primarily of just the blood pressure wave photocurrent signal which, after being integrated and passed through the unity gain amplifier 43 represents the envelope of the LED pulse current.

Between the LED pulses, the gate $G_7$ responsive to a gating pulse $\bar{\phi}_2$ is open or conductive from the node 25 to the lead 33 so that the parasitic capacitance does not charge during interpulse periods.

It should be noted that this blood pressure wave photocurrent signal, $i_3$ is divided in half by the split drains of the transistor $Q_3$, but is applied directly to the node 51 without amplification or conversion to a voltage parameter. It should also be noted that sunlight or ambient current in an amount several thousand times greater than the blood pressure wave current can be cancelled (subtracted) by the current $i_4$ at the node 51, leaving a signal current $i_5$ in the range of a few nanoamperes to be integrated across the holding capacitor $C_c$ of a few picofarads, thereby producing a signal in the millivolt range (10 to 50 mV) without amplification. This integrate and hold technique in accordance with the invention, makes possible fast recovery times from the sudden presence and resulting overload of the reflected IR steady state light pulse carrier as the finger is placed over the sensor. This overload is cancelled by the second-order feedback loop 39 (FIG. 1a) in times ranging from 1 or 2 seconds rather than 20 to 30 seconds, and eliminates the requirement for digital initialization commands. In another arrangement in accordance with the invention, the switch $G_2$ may be replaced by a suitable storage capacitor to hold the voltage on the node 50 during the $\phi_1$ or the ambient light cancellation period.

The switched capacitor transconductance element 40 will now be described in relation to the node 41 and the operational amplifier integrator 38 with reference to FIG. 3 as well as to FIGS. 1 and 1a. The object of the transconductance element 40 is to provide cancellation of any pulsed steady state synchronous light components with quick response time (1 to 2 seconds) even though the node 51 (FIG. 2) voltage may be driven to saturation, i.e., into overload. In overload, the element 40 responds with recovery times that are characteristic of the open loop response time ($R_A \cdot C_B$ rather than the closed loop response time $R_B \cdot C_B$). It should first be noted that one of the reasons for the fast open loop response, and a characteristic of the novel interconnection between the photodetector 12 and the second order synchronous feedback loop including the transconductance element 40, is that a small imbalance between the synchronous current components $i_1$ and $i_2$ will quickly drive the integrating capacitor $C_c$ to produce a high error voltage (nearly equal to the available supply voltage) for restoring the loop to balance.

The synchronous light cancellation loop 39 utilizes the transconductance element 40 comprised of a switched capacitor $C_E$ and two transmission gates $G_5$ and $G_6$. The voltage $VR_4$ is the reference voltage applied to the capacitor $C_E$ during the LED interpulse periods in response to the switching or gating pulses $\bar{\phi}_2$ and the voltage $V_f$ is the error voltage applied to the capacitor $C_E$ during the LED pulse periods in response to the switching or gating pulse $\phi_1$. This switched capacitor transconductance element 40 produces an output current $i_2$ at the node 41 (FIG. 1) proportional to the difference in the reference voltage $VR_4$ and the voltage $V_f$ from the integrating operational amplifier 42. The element 40 provides an equivalent transconductance $g_mE$ of $C_E/T$, where T is the switching period of the clock signal $\phi_4$, which is 13.67 milliseconds in this exemplary embodiment.

The feedback loop 39 in accordance with the invention is a second-order loop because it has two poles with the first pole being established by $(1/g_mE)(C_c)(R_A/R_B)$. The second pole is equal to $R_B C_B$ at the operational amplifier integrator 38. The feedback loop is a perfect second-order loop because the integrating operational amplifier 42 holds the error voltage at node 25 near $VR_4$ and the error voltage out of the unity gain amplifier 43 need not be increased to correct for an increase in steady state loop stress such as a change in steady state value of the pulse carrier amplitude or an imbalance of the correction provided by the ambient light cancellation circuit 32. This unique feature of the input loop allows it to be direct coupled to the pole-zero cancellation circuit without developing high DC offsets at the cancellation circuit output as might be the case in prior art systems where the input circuit was stressed with a high DC input current. The operational amplifier integrator 38 is similar to a conventional type except a phase lead is provided by the stabilization resistor $R_B$.

The ratio $R_B/R_A$ determines the high frequency attenuation feedback factor or the amplitude of the cancelling current $i_2$. It is to be noted that the differentiation time constant $R_B C_B$ of the feedback loop allows the high frequency components of the heart blood pressure envelope to be formed on the lead 25 as the output signal and that the loop acts to remove the low frequency motion artifact and components of the pressure envelope with the high pass time constant $T_H = R_B C_B$.

It is to be understood that this differentiation in the closed loop forward transfer function is a result of a low frequency integrating operation including $C_B$, $R_A$ and integrating operational amplifier 42 in the feedback or return path 39 of the perfect second-order control loop.

Just prior to the beginning of an LED pulse, nearly all of the current $i_3$ passing to the ambient light cancellation circuit 32 (FIG. 2) is photocurrent resulting from ambient light plus a current $i_6$ which is small bias current (a quiescent current from FET $Q_3$) flowing through the resistor $R_2$ (FIG. 1). At this time, the current $i_4$ is just equal to the input current $i_3/2$ in the "storage current mirror" 48 (FIG. 2). The resulting current difference $i_5$ is nearly zero until light pulses are reflected by a finger being positioned over the sensor 22 (FIG. 1).

A fraction of a second after a finger is placed over the sensor, i.e., over the LED and photodetector, the LED carrier cancellation current $i_2$ is still at its equilibrium value, but the voltage at node 37 (FIG. 1a) is quickly driven to a high saturation value by the samll error current $i_5$, which is just half of the photocurrent $i_1$ provided by the reflected LED light pulse carrier. As the holding capacitor $C_c$ is driven into saturation within a fraction of a second, nearly half of the total power supply voltage is applied at the output of the unity gain isolation amplifier 43 across the input resistor $R_A$ of the operational amplifier 42. Current resulting from this high fraction of supply voltage applied across the resistor $R_A$ flows through and charges the integrating capacitor $C_B$ in the feedback circuit of the operational amplifier 42. At some point in time, the charge across the capacitor $C_B$ reaches a value such that the output voltage $V_f$ from the amplifier 42 such that the current $i_2$ from the transconductance element 40 is equal to the reflected synchronous steady state LED light component of the current $i_1$. At this point in time, the voltage at the node 37 (FIG. 1a), i.e., across the holding capacitor $C_c$, starts to fall rapidly and the loop closes to reach equilibrium with a closed loop time constant determined largely by $R_B \cdot C_B$. This closed loop time constant is much shorter than the open loop time constant $R_A \cdot C_B$ since $R_A$ is usually approximately five to ten times $R_B$ for proper stabilization of the perfect second-order control loop.

Another function of the synchronous light cancellation loop 39 is to correct for any imbalance in the ambient light cancellation circuit 32 which, if not corrected, will produce a small residual component in the output $i_5$ passed to the integrate and hold section which is just the difference between the current $i_4$ and the exact current $i_3/2$ required for balance. Any such residual component will result in the holding capacitor $C_c$ charging, and the resulting error voltage will charge the integrating capacitor $C_B$ until any errors are perfectly cancelled out by a change in the current $i_2$. An important advantage of this second-order loop arrangement is that cancellation of $i_5$ imbalance current (and steady state pulse current) is achieved with negligible change in the DC differential input error voltage of the amplifier 42, and therefore the DC quiescent voltage at the output of the signal conditioning circuit 24 delivered to the amplifier and bandpass filter 26 (FIG. 1) is quite independent of large changes in ambient light conditions and held closely in value to the reference voltage $VR_4$.

Figure 4:
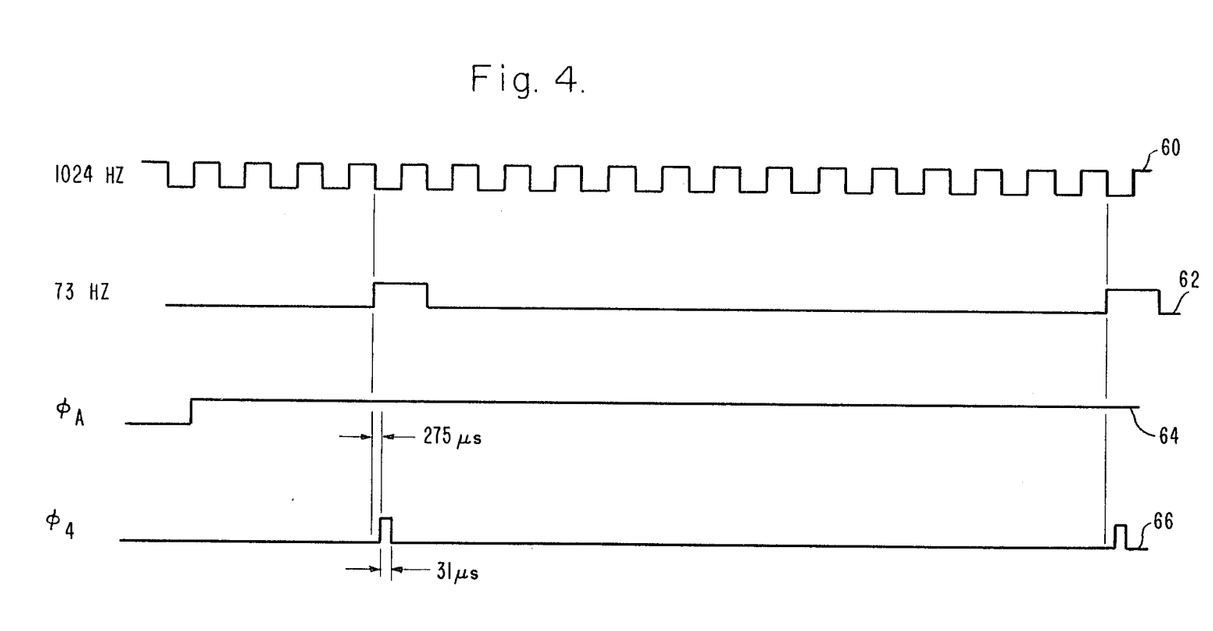
FIG. 4 is a basic logic timing diagram for the system of FIG. 1.

Referring now to the system timing diagram of FIG. 4, the clock pulse generated for the digital watch at nearly 32 kHz (actually 31,744 Hz) is first divided down to 1024 Hz, as shown by a waveform 60, and then further divided down by 14 to produce a low frequency clock at 73 Hz as shown by a waveform 62 for operation of the system in FIG. 1 as a heart pulse rate monitor. This lower rate controls the integrate and hold cycle, but only while the control signal $\phi_A$ of a waveform 64 is turned on by the operator when ready to measure heart pulse rate. The next and every 14th trailing edge (1 to 0 transition) of the 1024 Hz clock of the waveform 60 initiates a 275 μs delay. The LED is then turned on for 31 μs as shown by a waveform 66. The sequence of turning on the LED at this lower rate of 73 Hz continues until the operator has read the heart pulse rate and turns the control signal $\phi_A$ off.

Figure 5:
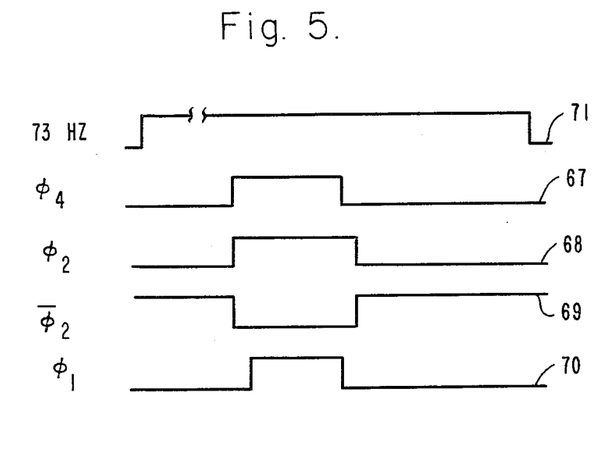
FIG. 5 is a specific logic timing diagram for the circuits of FIGS. 2 and 3.

Referring now also to FIG. 5, each time a $\phi_4$ pulse of a waveform 67 is generated, a $\phi_2$ pulse of a waveform 68 is generated. After a delay of about 0.1 s, a $\phi_1$ pulse of a waveform 70 is generated, the $\phi_1$ pulse being terminated at the end of the $\phi_4$ pulse. The $\phi_2$ pulse, and its compliment $\overline{\phi}_2$ of the waveform 69 terminates after the $\phi_4$ pulse terminates to complete a pulse wave current sampling cycle. This arrangement of turning on the LED for 31 μsec at a 73 Hz rate (i.e., about every 13.7 milliseconds as shown by a 73 Hz pulse of a waveform 71) conserves power, and allows ample time between LED pulses for the background noise signal to be measured and stored in the capacitor $C_D$ (FIG. 2). Referring now also to FIG. 2, when the pulse $\overline{\phi}_2$ is low (false), the gate $G_1$ stops conducting. Both of the gates $G_1$ and $G_2$ are then open (not conducting for about 0.1 μs). Then the $\phi_1$ pulse of the waveform 70 turns on the gate $G_2$ for control of the voltage at node 50 which would otherwise float, and also controls sampling and integrating of the reflected LED light pulse signal through the gate $G_3$ (FIG. 1a). It is to be noted that the gate $G_7$ is controlled by the pulse $\overline{\phi}_2$ of the waveform 69, so that the unity gain amplifier 43 will be disconnected prior to the sampling period $\phi_1$. The 0.1 μs delay in generating the $\phi_1$ pulse allows time for the gate $G_1$ to disconnect before shorting the node 50 to the voltage −V through the gate $G_2$, and the 0.1 μs delay in forming the $\overline{\phi}_2$ pulse after terminating the $\phi_1$ pulse, allows time for the shorting gate $G_2$ to disconnect before again starting to store a charge in the capacitor $C_D$ proportional to the ambient light after the LED pulse terminates.

The feedback loop of section 24 functions as a bandpass filter with a high pass time constant $T_H$ and a low pass time constant $T_L$ where:

$$T_L = \frac{1}{g_{mE}} \frac{R_A}{R_B} C_c$$

$$T_H = R_B C_B$$

The system upper corner frequency $\frac{1}{2}\pi T_L$ is well below any beat frequencies of sampling frequency harmonics and 120 Hz ambient light frequencies.

Figure 6:
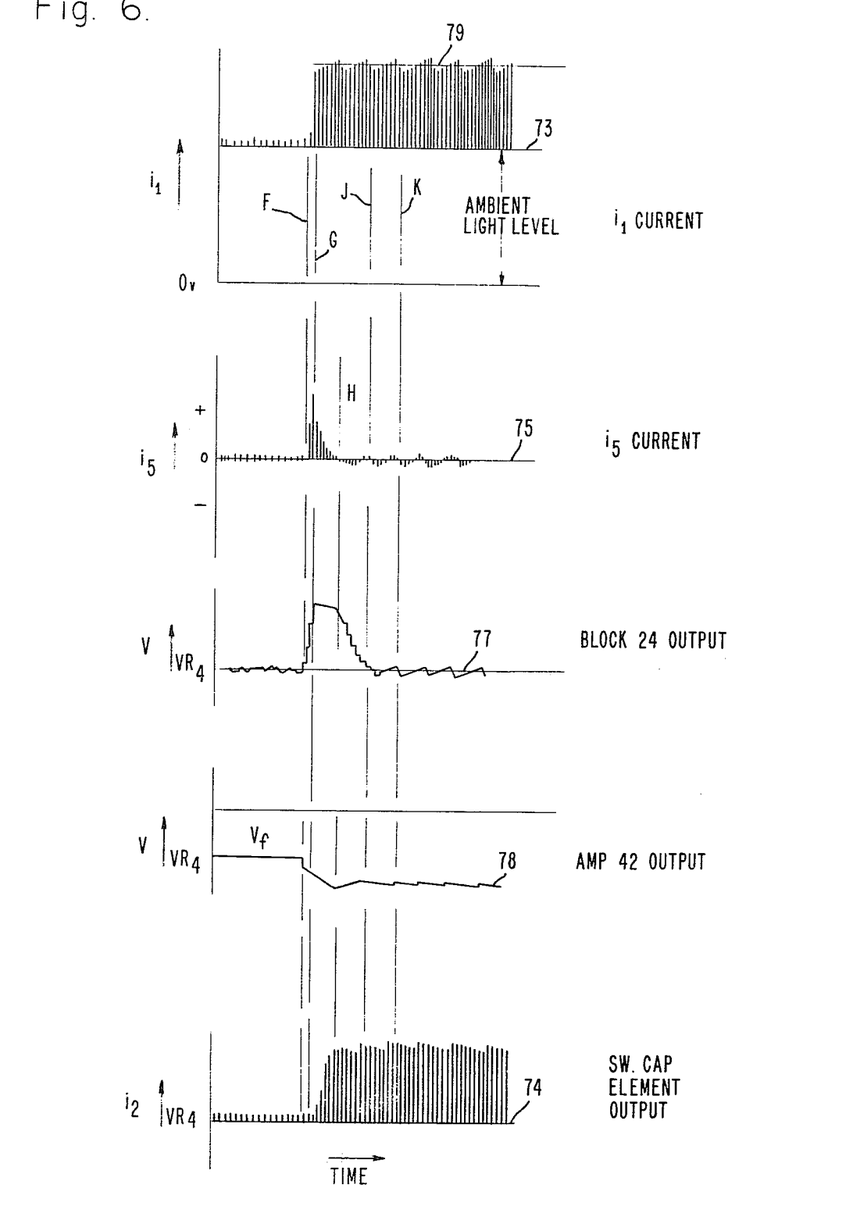

Referring now to FIG. 6 as well as to FIGS. 1 and 2, the system operation will be further explained including the operation of the second order control loop of the element 24. A waveform 73 shows the photodiode current $i_1$ and the ambient light current which is many times greater in amplitude than the current pulses. It is to be noted that the pulses of FIG. 6 which in the illustrated system are 13.67 milliseconds apart are shown with fewer pulses than actually occur during the illustrated time, for purposes of clarity of illustration. Prior to a time F, the photocurrent $i_1$ of the waveform 73 from the photodiode 12 consists of the ambient light level current plus a small amount of pulsed current from direct coupling between the IR LED 10 and the photodetector 12. The sensor can be constructed so that this current is quite small and in any case cancelled by the balancing current $i_2$ of a waveform 74 provided by the switched capacitor transconductance element 40. Thus, prior to the time F, the current $i_2$ of the waveform 74 removes the small steady state pulse carrier component and the ambient light component is removed by cancellation in the block 48 of FIG. 2. The resulting current $i_5$ of a waveform 75 has an average value of zero prior to time F. It is to be noted that the current $i_5$ pulses are one-half of the current pulse amplitude of $i_1$ in the absense of pulse cancellation. The output of the signal conditioning block 24 is provided by the unity gain amplifier 43 connected to integrate and hold capacitor $C_c$ which neither charges or discharges a significant amount at this time. The output of the amplifier 43 on the lead 25 therefore prior to time F is maintained as a steady state value around $VR_4$ with a small amount of flicker noise present as shown by a waveform 77.

At the time F, a finger is placed over the sensor 22 and within a small fraction of a second, the reflected IR pulse carrier has reached its full steady state value shown by the waveform 73 at a time G. The carrier cancellation current $i_2$ has not changed appreciately at the time G from its steady state value in this time interval from the time F as can be seen by the waveform 74. Consequently, at the time G, nearly the full amplitude carrier current (divided in two by the input split-drain device) is applied as the current $i_5$ to charge the integrate and hold capacitor $C_c$.

Because the capacitor $C_c$ need be only a few (2-4) picofarads and also because there are a few (3-4) picocoulombs in each carrier pulse, the integrate and hold capacitor $C_c$ output can be driven near the positive supply voltage +V limit by just a few (2-3) carrier pulses and the output at node 25 of the unity gain amplifier 43 following the capacitor $C_c$ is also driven near the positive supply voltage limit at the same time. Because the interval between pulses is only 13.7 ms, the output can be driven into saturation within a small fraction of a second as shown by the waveform 77. Also, because the reference voltage VR₄ is midway between the supply voltages (+V and −V), the output positive swing of the waveform 77 is nearly half the supply voltage and this voltage swing is applied across the resistor $R_A$ of FIG. 1 to discharge the integgrating capacitor $C_B$ at a high rate as shown in a waveform 78 by the rapid negative slewing as the output ($V_f$) of the integrating amplifier 42.

As the integrating amplifier 42 slews toward the negative supply, the switched capacitor transconductance element pulsed output current (or charge) of the waveform 74 increases in direct proportion to the difference $VR_4 - V_f$. At a time H, the pulsed output charge of the waveform 74 is just equal to the IR input carrier steady state value as shown by a level 79 of the waveform 73 representing the steady state level of the pulses. The i₅ pulsed charging current of the waveform 75 which is the difference between i₁ with ambient light removed and i₂, therefore reaches a zero value at time H and starts to swing negative. At this time, the capacitor $C_c$ begins to discharge away from the positive supply +V and the unity gain amplifier 43 comes out of saturation as seen by waveform 77. Thus, when the current i₃ is intense because of an uncancelled steady state pulse carrier, the voltage increases rapidly at node 25, the voltage $V_f$ falls rapidly and the i₂ current increases until the integrating capacitor $C_c$ charging current i₅ swings negative at the time H in the waveform 75, resulting in a rapid drop in the output of the unity gain amplifier 43.

The rapid drop in the output voltage of the unity gain amplifier 43 terminates the negative slew of integrating amplifier 42 as shown by the waveform 78. It is to be noted that the compensation resistor $R_B$ introduces phase lead and allows the output of the waveform 78 to assume a positive slope in advance of the time that the voltage drive across $R_A$ of the amplifier 42 has reached $VR_4$ near the time J as can be seen at the waveform 77. Therefore, the output voltage $V_f$ from the amplifier 42 is near a final or stabilized value at time J as shown by the waveform 78.

Although the front end circuitry is settled out by the time J, some additional time is required for the following amplifiers and bandpass filter (26) to settle or stabilize. This requirement of the bandpass filter is on the order of an additional 1-2 seconds so that the entire system is ready to detect the arrival of a systolic pressure wave at a time K.

Figure 7:
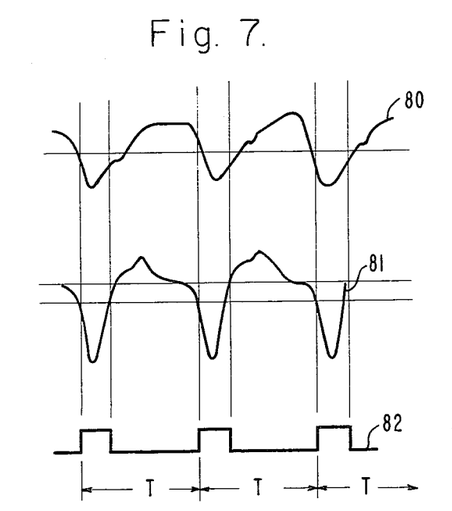
FIG. 7 is a schematic diagram of voltage as a function of time illustrating a typical systolic blood pressure waveform developed by the signal conditioning circuit (Block 24) and the amplifier and bandpass filter (Block 26) of FIG. 1; and the pulse train that is derived from the threshold disciminator (28) of FIG. 1.

A typical blood pressure waveform voltage of the waveform 77 after the time K as monitored by this integrate and hold technique at the rate of 73 Hz is shown in FIG. 7 by a waveform 80. Note that because the arrival of the pressure wave results in dialation of the capillaries and an increase in light absorption, the pressure rise (systolic) period is represented by a negative going voltage and is short compared to the pressure drop (diastolic) period. The signal conditioning section 24 performs both a short time constant (50 ms) integration and 480 ms differentiation on the true pressure waveform, but the time interval from one peak to the next remains exactly the same as for the true pressure waveform. The pulse of a waveform 81 is provided by the amplifier and bandpass filter 26 and because of the compensation provided by the pole zero cancellation has a shape relatively independent of the long time constant filtering in the section 24. Measuring the period T from one cycle to the next by detecting the peaks and timing the period between each peak of the waveform 81 thus yields a correct measurement of heart pulse rate, particularly if a running average (i.e., an average period over the last N cycles) is used to determine pulse rate as a reciprocal of the average period. Peak detection is best accomplished by the threshold discriminator 28 (FIG. 1) which converts the pressure wave voltage of the waveform 81, which is the pressure wave of the waveform 80 after amplification and bandpass filtering, to produce a pulse train of a waveform 82.

Period timing is then done by the digital watch timing and pulse rate computation section 18. The timing is done from leading edge to leading edge of each pulse in the pulse train. Pulse rate computation is simply the inverse of the average period measured, i.e., the result of the simple equation $R = I/T$. The rate thus computed is displayed and updated every 4 systolic intervals, for example, in such a manner as to allow each rate displayed to be clearly read before an update. If the pulse rate being monitored is steady, the average of N periods where N is typically 4, will yield an accurate and steady pulse rate reading. In practice, the operator may leave the system turned on until the rate displayed is steady, which should normally be within 10 seconds, or less.

Figure 9:
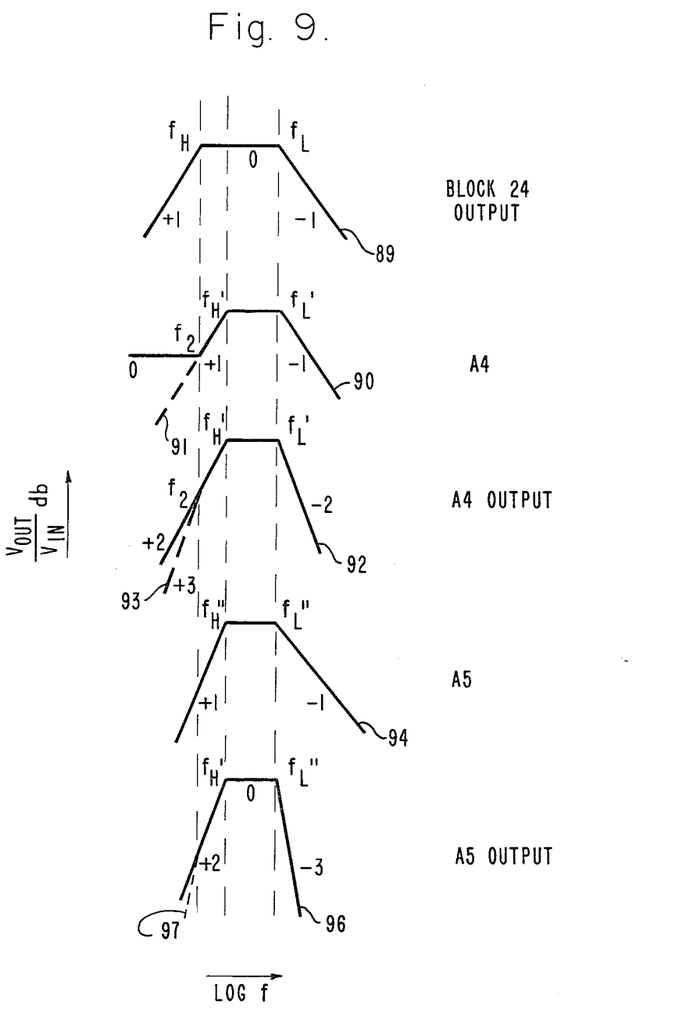
FIG. 9 is a schematic drawing of diagrams the output to input voltage ratio in decibles as a function of log f for explaining the amplifier and bandpass filter of FIG. 8.

The amplifier and bandpass filter 26 of FIG. 1, in accordance with the invention, may be the circuit as illustrated in FIG. 9 for compensating the filtering in block 24 so that the uncertainty in detecting the pulse rate at the discriminator 28 is decreased. The combination of the watch processing section 24 and the illustrated compensation arrangement as well as the compensating arrangement itself are the novel features in accordance with the subject invention. The illustrated amplifier and filter 26 includes stages 86 and 88 each providing differentiation and integration to respectively control the high pass ($f_H'$) and low pass ($f_L'$) corner frequencies of the passband. The signal from the block 24 at the node 25 is applied through a differentiating capacitor $C_1$ and a resistor $R_1$ to the negative input terminal of an operational amplifier $A_4$ having its positive input terminal coupled to the reference voltage $VR_4$. The signal at the output of the amplifier $A_4$ is fed back through a resistor $R_2$ and parallel coupled capacitor $C_2$ to the negative input terminal thereof. A compensating resistor $R_3$ is coupled in parallel with the capacitor $C_1$ for providing a zero at $f_2$ to cancel the pole at the high pass frequency $F_H$ resulting from the differentiation with time constant $T_H = R_B \cdot C_B$ in the block 24.

Figure 8:
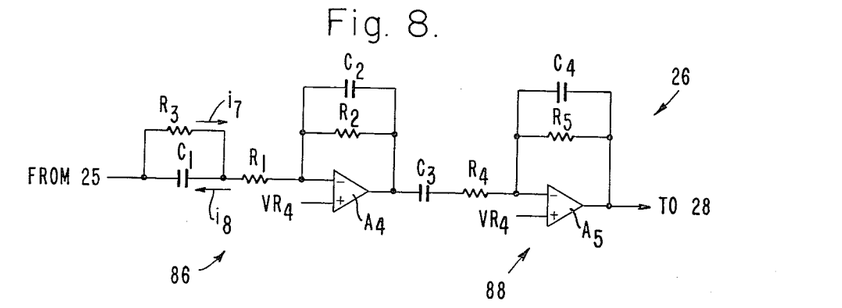
FIG. 8 is a schematic circuit and block diagram of an amplifier and bandpass filter of FIG. 1 including the pole-zero cancellation system in accordance with the invention.

The stage 88 includes a capacitor $C_3$ and a resistor $R_4$ serially coupled from the output terminal of the amplifier $A_4$ to a negative input terminal of an operational amplifier $A_5$, the latter amplifier having a positive input terminal coupled to the reference voltage $VR_4$. The signal at the output terminal of the operational amplifier $A_5$ is fed back to the negative input terminal through a parallel coupled resistor $R_5$ and a capacitor $C_4$. The amplified and filtered signal is applied from the output terminal of the amplifier $A_5$ to the discriminator 28.

Referring now also to FIG. 9, an asymptotic passband diagram 89 has a high pass corner frequency $f_H$ and a low pass corner frequency $f_L$ forming the passband at the output of the block 24. The high pass and low pass frequencies are:

$$f_H = \frac{1}{2\pi T_H} \text{ where } T_H = R_B C_B \text{ and}$$

-continued $$f_L = \frac{1}{2\pi T_L} \text{ where}$$

$$T_L = \frac{1}{g_m E} \frac{R_A}{R_B} C_c.$$

The characteristic output of the amplifier stage $A_4$ without the effect of the block 24 is shown by an asymptotic passband diagram 90 with a high pass corner frequency of $f_H' = (1/2\pi T_d)'$ where $T_d' = (R_1 \| R_3)C_1$. The high pass corner frequency $f_L'$ is selected with a greater value than the high pass corner frequency $f_H$ so that illustrated compensation may be provided. It is to be noted that the symbol means that $R_1$ and $R_3$ are in parallel. The diagram 90 has a low pass frequency $f_L' = (1/2\pi T_i)$ where $T_i = R_2 C_2$. Thus, the $C_1$, $R_1$, $R_3$ network determines the high pass frequency and the $R_2 C_2$ network determines the low pass frequency. At a frequency $f_2 = (1/2\pi T_3)$ where $T_3 = R_3 C_1$, the low frequency asymptote of the passband diagram 90 becomes flat to DC as shown by the solid line. The compensating resistor $R_3$ has the effect of adding a transmission zero which cancels the pole provided by the differentiation time constant $T_H$ of $R_B C_B$ in block 24. A dotted line 91 shows the low frequency asymptote if the compensating resistor $R_3$ were not included in the circuit. A passband diagram 92 at the output of the amplifier $A_4$ has a high pass asymptote that continues at a constant +2 slope as a result of the combination of the passband of the diagrams 89 and 90. A dotted line 93 shows a +3 slope of the low frequency asymptote which would occur if the compensating resistor $R_3$ were not utilized.

The $A_5$ individual stage characteristic is shown by a passband asymptotic diagram 94 and the $A_5$ composite output characteristic is shown by a passband diagram 96. The high pass and low pass frequencies of the diagrams 94 and 96 are respectively $f_H''$ and $f_L''$ where $f_H'' = (1/2\pi T_d'')$ and $f_L'' = 1/2\pi T_i''$. The time constant $T_d'' = R_4 C_3$ and the time constant $T_i'' = R_2 C_2$. It is to be noted that the high pass and the low pass frequencies of the diagram 96 may be represented by two zeros and five poles. A dotted line 97 having a +3 slope shows the attentuation that would be present in the absence of the compensating resistor $R_3$.

The following are illustrative values of the time constants that may be selected:

| | | | |
|---|---|---|---|
| $T_H$ | = | .48 | seconds |
| $T_L$ | = | .05 | seconds |
| $T_3$ | = | .48 | seconds |
| $T_d'$ | = | 0.1 | seconds |
| $T_i'$ | = | .05 | seconds |
| $T_d''$ | = | 0.1 | seconds |
| $T_i''$ | = | .05 | seconds |

The termination of the slope resulting from the differentiation at the stage 86, is a result of pole and zero cancellation. It is well known in the art that equal zero and pole terms in the respective numerator and denominator of a transfer function expression using complex notation will cancel. To further explain the slope termination, the differentiation action of $R_B C_B$ in the block 24 will provide a decaying positive voltage in the time domain following the systolic pressure wave and having the time constant $T_H$. During this decay, it is a well known property of an exponential R-C discharge that the slope (time rate of change) of the voltage will be porportional to the difference between the instantaneous value of the voltage and the quiescent or asymptotic value of the voltage. Stated in another way the ratio of the slope of the input voltage to the input voltage remains constant following an input disturbance. Since the current flow in $C_1$ ($i_8$ in FIG. 8) is proportional to the input voltage slope and opposite in direction to the current flow in $R_3$ ($i_7$ in FIG. 8) which is proportional to the input voltage, it is possible to select the value of $R_3$ such that $i_7$ is equal to and just cancels $i_8$ during the R-C decay. Thus, the zero cancellation of the block 24 pole $R_B \cdot C_B$ is performed by the action of the compensating resistor $R_3$ and the capacitor $C_1$.

The system transfer function provides a sharp cut-off of high frequency noise by the three poles at $f_L$, $f_L'$ and $f_L''$. Also, the system transfer function has a fairly sharp low frequency cut-off resulting from the two transmission zeros which remove low frequency noise and serve an even more important function which is to reject finger motion artifact. It is to be noted that susceptibility to finger motion is a primary limitation to the illustrated type of plethysmograph system. The pole-zero compensation although decreasing the sharpness of the low frequency cut-off, provides the equivalent of a two section low frequency filter which increases system signal-to-noise ratio beyond that obtainable with a three section filter and improves the overall system response to the heart blood pressure wave by eliminating certain overshoot components of the response which would be present in a system with three differentiators.

Figure 10:
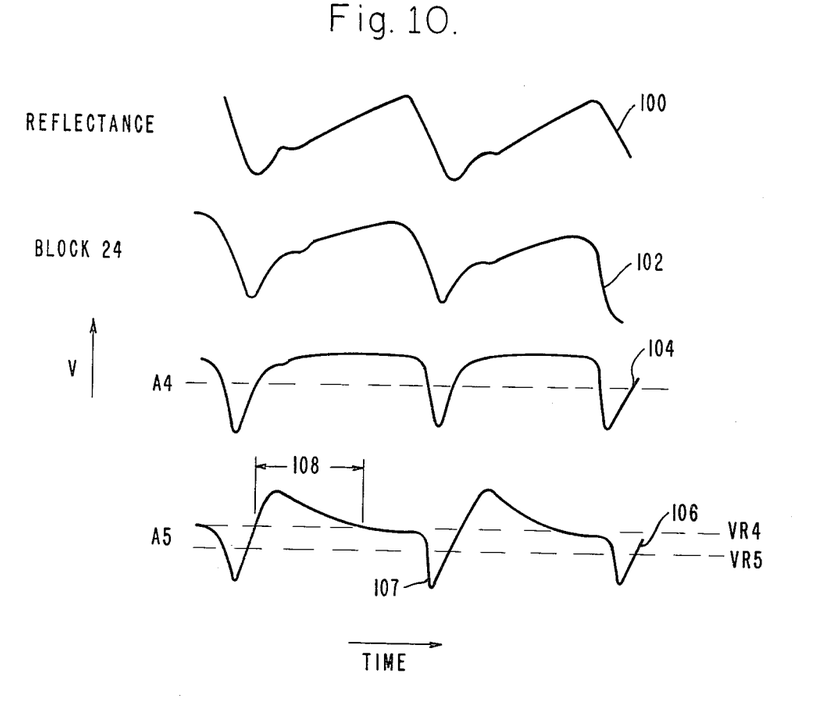
FIG. 10 is a schematic diagram of waveforms of voltage as a function of time for further explaining the operation of the amplifier and bandpass filter of FIG. 8 with the pole-zero cancellation system in accordance with the invention.

The improvement in system response can best be understood by referring also to the waveforms of FIG. 10 which shows an amplified and filtered heart pressure wave that reliably triggers the discriminator. A waveform 100 shows the reflectance signal resulting from the heart blood pressure modulation and a waveform 102 shows the heart blood pressure signal at the output of the block 24. The signal at the output of the amplifier $A_4$ with the pole zero cancellation of the resistor $R_3$ is shown by a waveform 104. The signal at the output of the amplifier $A_5$ is shown by a waveform 106 with the reference voltage level $VR_4$ and the trigger voltage level $VR_5$ at the discriminator 28. The pole zero cancellation deletes the effect of differentiation in the block 24 so that a heart blood pressure wave of the waveform 104 appears to be the result of a single differentiation of the photocurrent into the block 24 which was the original heart blood pressure amplitude modulation. A long time constant differentiation ($R_B C_B$) in the block 24 is now replaced by a short time constant differentiation ($R_1 \| R_3 \cdot C_1$) at the stage 86. After the second differentiation at the input of amplifier $A_5$, the $A_5$ output being shown by the waveform 106, this second short time constant differentiation returns the voltage waveform rapidly to the amplifier $A_5$ quiescent output voltage which is $VR_4$ and therefore upon arrival of the next systolic pressure wave such as 107, the signal crosses the discriminator trip voltage threshold $VR_5$ with a fast or steep slope. The timing sensitivity to motion artifact is reduced by the steep slope of the leading edge of the systolic pulse 107 in comparison to a gradual slope which provides more sensitivity to motion artifact because the time position of the signal crossing the trigger voltage $VR_5$ is more severly modulated by motion artifact signals. Also, the second differentiation of the waveform 106 provides a highly predictable starting voltage by rapidly returning the $A_5$ output to the baseline voltage ($VR_4$). It should be noted that at higher rates, the starting points will move closer to the back kick such as at 108 produced by the preceding pulse so that the systolic pulse starting voltage is displaced from the voltage $VR_4$. However, at higher pulse rates, especially those produced by exercise, the heart rhythm generally becomes more uniform so that the displacement of the starting voltage displacement from $VR_4$ is uniform and has substantially no contribution on a beat-to-beat basis.

Laboratory investigations based on a four interval pulse average have shown that a 5-10 PPM (Pulses Per Minute) uncertainty can be expected with a single slow integration and differentiation arrangement and a 3-5 PPM uncertainty can be expected with an uncompensated triple differentiation of the illustrated system without the resistor $R_3$. Tests have shown that with the two differentiator pole zero compensation of the preferred embodiment, only a 1-2 PPM uncertainty is to be expected.

In the illustrated system, it is desirable to have $R_BC_B$ very large to decrease, at the amplifier $A_4$, the ratio of DC gain to AC gain, that is $(R_3/R_1)$ should be a large ratio to insure wide DC operating margins. The time constants $T_H$ and $T_3$ must be equal, that is, $R_BC_B$ must equal $R_3C_1$. In a hybrid circuit layout, such as in a watch, the size of the capacitor $C_B$ is limited. The value of $R_B$ is limited by the minimum allowable value of the low pass frequency $f_L$, which if too small, will restrict the passage of desired high signal frequency components through the front end (block 24). The maximum value of the resistor $R_3$ is therefore constrained by two front end requirements as well as the limited maximum value of the capacitor $C_1$. Thus, the long time constant in the block 24 is required to maintain proper system DC operating margins and the pole-zero cancellation provides improved dynamic characteristics in terms of pulse response and signal-to-noise performance.

Although particular embodiments of the invention have been described and illustrated herein, it is recognized that modifications and variations may readily occur to those skilled in the art and consequently, it is intended that the claims be interpreted to cover such modifications and equivalents.

What is claimed is:

1. A pulse rate measuring system for receiving during sample pulse intervals, a pulsed photocurrent signal including an ambient light and a reflected light carrier signal which is amplitude modulated by a heart blood pressure signal comprising:

signal processing means responsive to said pulsed photocurrent signal and including a second order loop having a first differentiator means providing a transfer function having a high pass pole at a first frequency, cancellation means for forming a zero at said first frequency to cancel the high pass pole of said transfer function; and second differentiator means coupled to said cancellation means for forming a high pass pole at a second frequency, and additional pulse-shaping and output means coupled to said second differentiator means.

2. The combination of claim 1 in which said second differentiator means includes means to provide said second frequency greater than said first frequency.

3. The combination of claim 2 in which said second differentiator means includes a series coupled capacitor and a resistor and said cancellation means includes a bypass resistor coupled in parallel with the capacitor of said second differentiator means.

4. The combination of claim 3 in which said first differentiator means has a first time constant and said second differentiator means is selected to provide a second time constant substantially shorter than said first time constant.

5. The combination of claim 4 further including an operational amplifier coupled to the series coupled resistor of said second differentiator means.

6. The combination of claim 1 in which said signal processing means includes ambient light cancellation means, first integrator means coupled between said ambient light cancellation means and said cancellation means and feedback means coupled to said first integrator means and to said light cancellation means, said feedback means including second integrator means and a switched transconductance element, said second integrator means including an operational amplifier with said first differentiator means coupled between an input terminal and an output terminal of said operational amplifier.

* * * * *